United States Patent [19]
Farrar et al.

[11] Patent Number: 5,849,762
[45] Date of Patent: Dec. 15, 1998

[54] PERIPHERALLY ACTING ANTI-PRURITIC OPIATES

[75] Inventors: John J. Farrar, Chester Springs; Alan Cowan, Ambler, both of Pa.

[73] Assignee: Adolor Corporation, Malvern, Pa.

[21] Appl. No.: 892,194

[22] Filed: Jul. 14, 1997

[51] Int. Cl.⁶ .................................................. A61K 31/445
[52] U.S. Cl. ............................................................. 514/327
[58] Field of Search ............................................. 514/327

[56] References Cited

U.S. PATENT DOCUMENTS

| | | |
|---|---|---|
| 3,714,159 | 1/1973 | Janssen et al. . |
| 3,884,916 | 5/1975 | Janssen et al. . |
| 3,996,214 | 12/1976 | Dajani et al. . |
| 4,012,393 | 3/1977 | Markos et al. . |
| 4,025,652 | 5/1977 | Diamond et al. . |
| 4,060,635 | 11/1977 | Diamond et al. . |
| 4,066,654 | 1/1978 | Adelstein et al. . |
| 4,069,223 | 1/1978 | Adelstein . |
| 4,072,686 | 2/1978 | Adelstein et al. . |
| 4,103,668 | 8/1978 | Adelstein et al. . |
| 4,115,564 | 9/1978 | Diamond et al. . |
| 4,116,963 | 9/1978 | Adelstein . |
| 4,125,531 | 11/1978 | Yen . |
| 4,194,045 | 3/1980 | Adelstein . |
| 4,203,920 | 5/1980 | Diamond et al. . |
| 4,277,605 | 7/1981 | Buyniski et al. . |
| 4,326,074 | 4/1982 | Diamond et al. . |
| 4,326,075 | 4/1982 | Diamond et al. . |
| 4,533,739 | 8/1985 | Pitzele et al. . |
| 4,824,853 | 4/1989 | Wals . |
| 4,990,521 | 2/1991 | Van Daele et al. . |
| 5,116,847 | 5/1992 | Gilbert et al. ................. 514/327 |
| 5,236,947 | 8/1993 | Calvet et al. . |
| 5,242,944 | 9/1993 | Park et al. . |
| 5,348,744 | 9/1994 | Kurazumi et al. . |

FOREIGN PATENT DOCUMENTS

WO 95/27510  10/1995  WIPO .

OTHER PUBLICATIONS

Medline Abstract, AN:94265060, Farouk, R. et al, Apr. 1994.
Farouk, R. et al., British Journal of Surgery, 81(4), 603–606 [England].
McMahon et al., TINS, vol. 15, No. 12 (1992).
Bernstein et al., Journal of Investigative Dermatology, 78: 82–83 (1982).
Ballantyne et al., Pain, 33: 149–160 (1988).
J. D. Bernhard, J. Am. Acad. Derm. 24: 309 (1991).
IASP Newsletter, Sep./Oct. 1996, Magerl, pp. 4–7.
Thomas et al., Brain Research, 695: 267–270 (1995).

*Primary Examiner*—Marianne M. Cintins
*Assistant Examiner*—M. Moezie
*Attorney, Agent, or Firm*—Imre Balogh

[57] ABSTRACT

Anti-pruritic compositions and methods of using the compositions for the prevention or treatment of pruritus comprising:

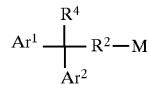

wherein M is

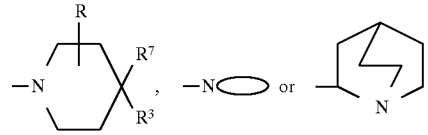

wherein:

R, $R^2$, $R^3$, $R^4$, $R^7$, $Ar^1$ and $Ar^2$ are as defined in the specification in a pharmaceutically acceptable carrier.

3 Claims, No Drawings

PERIPHERALLY ACTING ANTI-PRURITIC OPIATES

BACKGROUND OF THE INVENTION

1. Field of the Invention

This invention relates to peripherally acting anti-pruritic opiates having substantially no effects on the central nervous system and method of topically treating pruritic conditions therewith.

2. Reported Developments

The prior art has investigated the physiology and treatment of pruritus as illustrated hereunder.

Itch is a well known sensory state associated with the desire to scratch. As with pain, itch can be produced by a variety of chemical, mechanical, thermal or electrical stimuli. In addition to the difference in the sensory quality of itch and pain, they also differ in that (1) itch, unlike pain, can only be evoked from the superficial layers of skin, mucosa, and conjunctiva, and (2) itch and pain usually do not occur simultaneously from the same skin region; in fact, mildly painful stimuli, such as scratching, are effective in eliminating itch. In addition, the application of histamine to skin produces itch but not pain. Itch and pain are further dissociated pharmacologically: itch appears to be insensitive to opiate and non-steroidal anti-inflammatory drug (NSAID) treatment, both of which are effective in treating pain.

Although itch and pain are of a class in that both are modalities of nociception transmitted by small unmyelinated C fibers, evidence that itch is not just a variety of low-threshold pain is overwhelming. Itch leads to the reflex or urge to scratch; pain leads to withdrawal. Removal of the epidermis eliminates itch but causes pain. Analgesics, particularly opiods, relieve pain but often cause itch (see, for example *J. Am. Acad. Derm.* 24: 309–310, 1991). There can be no doubt that itching is of eminent clinical importance; many systemic and skin diseases are accompanied by persistent or recurrent itch attacks. Current knowledge suggests that itch has several features in common with pain but exhibits intriguing differences as well (see, for example, W. Magerl, *IASP Newsletter*, pp. 4–7, September/October 1996). McMahon et al (*TINS*, VoL 15, No. 12, pp. 497–501, 1992) provides a description of stimuli (Table a) and a comparison of the established features of itch and pain (Table b):

Table a

Stimuli that can elicit or augment itch

Physical

Mechanical. Light touch, pressure, suction.

Thermal Warming.

Electrical. Focal transcutaneous repetitive stimulation, transcutaneous constant current stimulation, intraneural microstimulation.

Chemical

Non-specific irritants. Acids, alkalis.

Inflammatory mediators. Histamine, kallikrein, bradykinin, prostaglandins.

Histamine-releasing substances. Compound 48/80, protamine, C3a.

Peptidases. Mucunain, papain, trypsin, mast cell chymase.

Neuropeptides. Substance P, vasoactive intestinal polypeptide, neurotensin, secretin.

Opioids. Morphine, β-endorphin, enkephalin analogues

TABLE b

Comparison of the established features of itch and pain

|  | ITCH | PAIN |
|---|---|---|
| Psychophysiology | | |
| Tissue | Skin. Mucous membranes | Most tissues |
| Stimulus | See Table a | Many stimuli |
| Intraneural microstimulation | Occasionally | Yes |
| Secondary sensations | Allokinesis (itchy skin) | Hyperalgesia |
| Psychogenic modification | Pronounced | Present |
| Counterstimuli | Scratching, pain, cooling | Tactile stimuli, cooling |
| Neurophysiology | | |
| Primary afferent neurons | C- and Aδ-fibres | C- and Aδ-fibres |
| Flare size | Large | Small |
| Spinal pathway | Anterolateral funiculus | Anterolateral funiculus |
| Protective reflexes | Scratching, sneezing | Flexion, guarding |
| Autonomic reflexes | Yes | Yes |
| Pharmacology | | |
| Capsaicin sensitivity | Yes | Chemogenic pain; yes |
| NSAID sensitivity | Probably not | Yes |
| Morphine sensitivity | No | Yes |

Abbreviation: NSAID, non-steroidal anti-inflammatory drugs.

Experimental focal itch stimuli are surrounded by a halo of seemingly unaffected tissue where light tactile stimuli are capable of eliciting itch-like sensations. The term itchy skin or allokinesis has been coined for these secondary sensations that are reminiscent of the features of secondary hyperalgesia evolving around a painful focus. A crucial observation is that itch and pain usually do not coexist in the same skin region and a mild noxious stimulus such as scratching is in fact the singly most effective way to abolish itch. This abolition of itch can be prolonged producing an 'antipruritic state'. Although mild scratch is often not painful, microneurographic recordings from humans have directly determined that such stimuli are among the most effective ways to excite cutaneous unmyelinated nociceptive afferents. (See, for example:

Shelly, W. B. and Arthur, R. P. (1957) *Arch. Dermatol.* 76,296–323;

Simone, D. A. et al. (1987) *Somatosens. Res.* 5, 81–92;

Graham, D. T. , Goodell, H. and Wolff, H. G. (1951) *J. Clin. Invest.* 30, 37–49;

Simone, D. A., Alreja, M. and LaMotte, R. H. (1991) *Somatosens, Mot. Res.* 8, 271–279;

Torebjörk, E (1985) *Philos. Trans. R. Soc. London Ser.* B 308, 227–234; and

Vallbo, A. B., Hagbarth, K. E., Torebjörk, H. E. and Wallin, B. G. (1979) *Physiol. Rev.* 59, 919–957).

Physiologically, there is evidence that substance P released from nociceptor terminals can cause the release of histamine from mast cells. Activation of mast cells, with release of the pruritogen histamine, occurs in immediate type hypersensitivity diseases, such as anaphylactic reactions and urticaria. Urticarial eruptions are distinctly pruritic and can involve any portion of the body, and have a variety of causes beyond hypersensitivity, including physical stimuli such as cold, solar radiation, exercise and mechanical irritation. Other causes of pruritus include: chiggers, the larval form of which secretes substance that creates a red papule that itches intensely; secondary hyperparathyroidism associated with chronic renal failure; cutaneous larva migrans, caused by burrowing larvae of animal hookworms; dermal myiasis, caused by maggots of the horse botfly, which can afflict horseback riders; onchocerciasis ("river blindness") caused by filarial nematodes; pediculosis, caused by lice infestations; enterobiasis (pinworm) infestations, which afflict about 40 million Americans, particularly school children; schistosome dermatitis (swimmer's itch); psoriasis; poison ivy and asteatotic eczema ("winter itch"). The role of histamine or other endogenous pruritogens in mediating itch associated with these and other pruritic conditions, such as atopic dermatitis, its not yet well established. For atopic dermatitis, in particular, it appears that itch is not inhibited by antihistamines, but by cyclosporin A, a drug which inhibits the production of cytokines which have been proposed as potential pruritogens.

Current therapies for the treatment of itch include a variety of topical and systemic agents, such as steroids, antihistamines, and some psychotherapeutic tricyclic compounds, such as doxepin hydrochloride. Many such agents are listed in *PDR Generics* (see Second Edition, 1996, p. cv for a listing of said agents). The limitations of these agents are well known to medical practitioners, and are summarized in the "Warnings" and "Precautions" sections for the individual agents listed in *PDR Generics*. In particular, the lack of complete efficacy of antihistamines is well known, but antihistamines are frequently used in dermatology to treat pruritus due to urticaria, atopic dermatitis, contact dermatitis, psoriasis, and a variety of other conditions. Although sedation has been a frequent side effect of conventional systemically administered antihistamines, a new generation of antihistamines has been developed that are nonsedating, apparently due to their inability to cross the blood-brain barrier.

Intravenous administration of opiate analgesics, such as morphine and hydromorphone has been associated with pruritus, urticaria, other skin rashes, and wheal and flare over the vein being injected. These itch and itch-related reactions are believed to be due to a histamine-releasing property of these opiates, via mast cell degranulation. These opiates are thought to act upon the mu subtype of opiate receptor, but the possibility of interactions at the other principal opiate receptor subtypes (delta and kappa) cannot be excluded since these and other pruritogenic analgesics are not pure mu agonists. The cellular loci of the receptor type(s) mediating the itching effect is not known, although the mast cell is a possible candidate since opiates cause histamine release from these cells. However, some investigators have suggested that the frequent inability of antihistamines to block morphine-induced itching suggests a non-histaminergic mediation of opiate-induced itching—mechanism which could involve central opiate receptors. Although i.v. morphine only occasionally results in generalized itching (in about 1% of patients), pruritus is more prevalent in opiate analgesia with epidural (8.5%) or intraspinal (45.8%) administration. (See, for example: Bernstein et al., "Antipruritic Effect of an Opiate Antagonist, Naloxone Hydrochloride", *The Journal of Investigative Dermatology*, 78:82–83, 1982; and Ballantyne et al, "Itching after epidural and spinal opiates", Pain, 33: 149–160, 1988.)

To date, treatment with opiates has not only proven useless in the treatment of itch, but appears to exacerbate itch in mammals. The consistent findings from human studies indicate that whether by central or peripheral mechanisms, opiates appear to promote rather than prevent itching, and that opiate antagonists have antipuritic activity.

Human clinical studies have generally shown that opiates cause itching and there is evidence that these effects can be reproduced in animal models, where itching sensations per se cannot be reported, but scratching behavior can be observed. (See, for example: Thomas et al., "Microinjection of morphine into the rat medullary dorsal horn produces a dose-dependent increase in facial-scratching", *Brain Research*, 695: 267–270, 1996; Thomas et al., "Effects of central administration of opioids on facial scratching in monkeys", *Brain Res.*, 585: 315–317, 1992; and Thomas et al., "The medullary dorsal horn: A site of action of opioids in producing facial scratching in monkeys", *Anesthesiology*, 79: 548–554, 1993).

Certain opiates, such as loperamide [i.e., 4-(p-chlorophenyl)-4-hydroxy-N-N-dimethyl-α,α-diphenyl-1-piperidinebutyramide hydrochloride] and its analogs were reported to be devoid of CNS effects, which is believed to be due to the failure of the opiates to cross the blood brain barrier. Loperamide HCl has been used for a long time in antidiarrheal formulations and has been completely free of the undesirable CNS effects.

We have now surprisingly discovered that certain opiates, which are substantially devoid of central nervous system effects, possess anti-pruritic activity.

SUMMARY OF THE INVENTION

In one aspect, the present invention provides compositions containing one or more compounds that exert anti-pruritic activity via peripheral opiate receptors but do not exhibit substantial CNS, CNS-mediated analgesic or systemic effects. In another aspect, the present invention provides methods involving the administration of the compositions to a mammal for the prevention or treatment of pruritus.

DETAILED DESCRIPTION OF THE INVENTION

The Anti-Pruritic Compounds

The compounds for use in the compositions and methods herein possess peripheral anti-pruritic and substantially no CNS activities because they do not cross the blood brain barrier. The failure to cross the blood brain barrier precludes the occurrence of the CNS systemic side effects, so that there is no potential for abuse. The compounds intended for use in the methods and compositions provided herein include any compound that by virtue of its interaction, either directly or indirectly, with peripheral opioid receptors ameliorates the peripheral hyperalgesic state, but does not exhibit systemic CNS-mediated analgesic activity or CNS side effects, including heaviness of the limbs, flush or pale complexion, clogged nasal and sinus passages, dizziness, depression, respiratory depression, sedation and constipation. These compounds include antidiarrheals that act as antidiarrheals via interaction, with μ, δ, or κ receptors, and opiate agonists, such as metkephamide and related enkephalin analogs. The compounds of the present invention, the description of which follows, have been reported in prior art patents all of which are incorporated herein by reference:

(a) Loperamide, its analogs, and its related compounds, metabolites and prodrugs thereof reported in U.S. Pat. Nos.

| | |
|---|---|
| 3,714,159 | 4,125,531 |
| 3,884,916 | 4,194,045 |
| 3,996,214 | 4,203,920 |
| 4,012,393 | 4,277,605 |
| 4,013,668 | 4,326,074 |
| 4,025,652 | 4,326,075 |
| 4,060,635 | 4,533,739 |
| 4,066,654 | 4,824,853 |
| 4,069,223 | 4,990,521 |
| 4,072,686 | 5,236,947 |
| 4,115,564 | 5,242,944 |
| 4,116,963 | |

Such compounds include compounds of Formula I; its N-oxide or a pharmaceutically acceptable salt or acid:

$$Ar^1 \underset{Ar^2}{\overset{R^4}{-}} R^2 - M \qquad \text{I}$$

wherein M is $$-N\underset{R^3}{\overset{R}{\diagup}} \underset{R^7}{\diagdown}, \quad -N\bigcirc \quad \text{or} \quad \text{[azabicycle]}$$

wherein:

$-N\bigcirc$ is an azabicycloalkyl containing from 6 to 9 atoms with at least 5 atoms in each ring and is unsubstituted or substituted with $OR^{18}$ in which $R^{18}$ is hydrogen or lower alkanoyl containing 2 to 7 carbons and $OR^{18}$ is at the 5 position in 5-membered rings or the 5 or 6 position in 6-membered rings and is attached in the endo or exo configuration;

$Ar^1$ and $Ar^2$ are either (i) or (ii) as follows:

(i) each is independently selected from aryl and heteroaryl groups containing from 5 to 7 members in the ring, each is unsubstituted or substituted with one or more substituents selected from halo, haloalkyl, hydroxy, alkyl, alkyloxy, aminosulfonyl, alkylcarbonyl, nitro, haloalkyl, trifluoromethyl, amino, aminocarbonyl, phenylcarbonyl or thienyl, where the alkyl groups are straight or branched chains lower alkyl containing from 1 to 6 carbon atoms; or (ii) $Ar^1$ and $Ar^2$ are each independently phenyl or pyridyl groups and with the carbon to which they are commonly linked form a fused ring so that the compounds of formula (I) have the structure:

[structure showing fused tricyclic system with M, $R^2$, $R^4$ and $(CH_2)_n$ bridge]

wherein n is 0 to 3;

$R^2$ is either alkyl in which the alkyl group is a straight or branched chain having 1 to 12 carbon atoms, or is alkylene having 1 to 6 carbon atoms with one or two double bonds;

$R^3$ is $Ar^3$, $-Y-Ar^3$, where Y is alkylene or alkyl having 1 to 3 carbon atoms, or is $$-\underset{R^8}{N}-\overset{O}{\overset{\|}{C}}-Ar^4;$$

$R^8$ is hydrogen or alkyl that is a straight or branched chain containing from 1 to 6 carbon atoms;

$Ar^3$ is aryl or heteroaryl containing from 5 to 7 members in the ring, which is unsubstituted or substituted with one or more substituents of halo, halo lower alkyl or lower alkyl;

$Ar^4$ is either:

(i) is a heterocycle containing one to three fused rings or which is unsubstituted or substituted with one or more substituents selected from halo, halo lower alkyl or lower alkyl, or (ii) $Ar^4$ is a radical of formula:

[phenyl ring substituted with $R^{10}$, $R^{11}$, $R^{12}$]

in which $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamnino, alkylcarbonylamino, alkylcarbonyl, alkylcarbonyloxy, aminosulfonyl, alkylsulfinyl, alkylsulfonyl, aLkylthio, mercapto, $C_3$–$C_6$ alkenyloxy, arylalkyloxy, aryloxy or alkyl, in which each group is unsubstituted or substituted with one or more halo atoms, halo alkyl or alkyl, and the alkyl groups are straight or branched chains that are lower alkyl;

R is hydrogen, alkyl, halo, haloalkyl or $OR^9$;

$R^9$ is selected from alkyl, arylalkyl, alkylcarbonyl, aminoalkyl, alkylaminoalkyl or dialkylaminoalkyl, in which the alkyl groups are straight or branched chains containing 1 to 12 carbon atoms;

$R^4$ is selected from among:

(i) 5- to 7-membered aryl groups, which are unsubstituted or substituted with lower alkyl, halo lower alkyl or halo, or (ii) heterocyclic rings, containing one to three heteroatoms, that are unsubstituted or substituted with halo, halo lower alkyl or lower alkyl, or (iii) alkyl containing from 1 to 8 carbon atoms, alkenyl containing 3 to 6 carbon atoms, cycloalkyl containing from 3 to 6 carbon atoms, cycloalkyl alkyl in which the first alkyl contains 3 to 6 carbons and the second containing 1 to 3 carbons, or cycloalkenyl containing 4 to 7 carbons, or $$-\overset{O}{\overset{\|}{C}}-N\underset{R^6}{\overset{R^5}{\diagup}} \qquad \text{(iv)}$$

where $R^5$ and $R^6$ are either:

(i) independently selected from hydrogen, alkyl, which is a straight or branched chain containing 1 to 12 carbon atoms, alkenyl, which is straight or branched chain, containing 1 to 12 carbon atoms and one or two double bonds, or aryl which contains 5 to 7 carbon atoms, or (ii) $R^5$ and $R^6$ are selected from carbon chains, heteroatoms, and carbon chains containing one or more heteroatoms, so that with the nitrogen atoms to which each is attached they form a 3- to 7-membered heterocyclic ring containing one to three heteroatoms that is unsubstituted or substituted with halo, halo lower alkyl or lower alkyl; and R$^7$ is selected from among:

H;

OH;

—R$^{14}$OR$^{13}$ in which R$^{13}$ is hydrogen or lower alkyl, alkanoyl containing 2 to 5 carbon atoms, and R$^{14}$ is lower alkenyl or lower alkyl;

—CH$_2$NR$^{15}$R$^{16}$ in which R$^{15}$ is hydrogen, lower alkyl or lower alkanoyl and R$^{16}$ is hydrogen or lower alkyl;

OR$^{15}$;

R$^{22}$OR$^{13}$, in which R$^{22}$ is lower alkyl;

—C(O)OR$^{17}$ in which R$^{17}$ is hydrogen, alkyl containing form 1 to 7 carbons or alkenyl having 3–7 carbon atoms, aryl or heteroaryl; or an alkali metal or alkaline earth metal salt.

The nomenclatures are to be understood to have the meaning generally understood by those skilled in the art as defined herein:

"Halogen" or "halide" or "halo" refers to F, Cl, Br or I, and also pseudohalides. In preferred embodiments halo refers to F, Cl, Br and I.

Pseudohalides are radicals that behave substantially similar to halides. Such radicals can be used in the same manner and treated in the same manner as halides (X, in which X is a halogen, such as Cl or Br). Pseudohalides include, but are not limited to cyanide, cyanate, thiocyanate, selenocyanate, azide and trifluoromethyl. As used herein, carbon chains and carbon chains with heteroatoms may be straight or branched or, if they contain 3 or more members, may be cyclic.

Alkyl, alkenyl and alkynyl carbon chains, if not specified contain from 1 to 20 carbons, preferably 1 to 12 carbons and are straight or branched.

Lower alkyl, lower alkenyl, and lower alkynyl refer to carbon chains having one to about 6 carbons. In preferred embodiments of the compounds provided herein that includes alkyl alkenyl, or alkynyl portions include lower alkyl lower alkenyl and lower alkynyl portions. Preferred among lower carbon chains are those having 1–3 carbons.

Aryl refers to cyclic groups containing from 3 to 15 or 16 carbon atoms, preferably from 5 to 10, more preferably 5 to 7 carbons. Aryl groups include, but are not limited to, groups such as phenyl, substituted phenyl, naphthyl, substituted naphthyl, in which the substituent is lower alkyl, halo, halo lower alkyl or lower alkoxy. Preferred aryl groups are lower aryl groups that contain less than 7 carbons in the ring structure.

Cycloalkyl refers to saturated cyclic carbon chains; cycloalkyenyl and cycloalkynyl refer to cyclic carbon chains that include at least one unsaturated triple bond. The cyclic portions of the carbon chains may include one ring or two or more fused rings.

Carbocyclic group is a ring containing at least three carbons; a heterocyclic group is a ring containing at least one carbon and one or more heteroatoms, preferably selected from among O, S and N, more preferably N and O. A heteroaryl group is an unsaturated ring structure containing 1 or more, preferably 1 to 3 heteroatoms in the ring. The rings may be single or two or more fused rings. Heteroaryl is used interchangeably with heterocycle.

Heterocycle refers to ring structures that include at least one carbon atom and one or more atoms, such as N, S, and O.

Alkyl refers to non-aromatic carbon chains that contain one or more carbons; the chains may be straight or branched or include cyclic portions or be cyclic.

Alicyclic refers to aryl groups that are cyclic.

Haloalkyl refers to an alkyl radical, preferably lower alkyl, in which one or more of the hydrogen atoms are replaced by halogen including, but not limited to, chloromethyl, trifluoromethyl, 1-chloro-2-fluoroethyl and other such groups. Halo lower alkyl refers to lower alkyl substituted with one or more halo substituents, and is preferably trichloromethyl or trifluoromethyl.

Haloalkoxy refers to RO— in which R is a haloalkyl group.

Aminocarbonyl refers to —C(O)NH$_2$.

Alkylaminocarbonyl refers to —C(O)NHR in which R is hydrogen, alkyl, preferably lower alkyl or aryl, preferably lower aryl.

Dialkylaminocarbonyl refers to —C(O)NR'R in which R' and R are independently selected from alkyl or aryl, preferably lower alkyl or lower aryl; carboxamide: refers to groups of formula NR'COR.

Alkoxycarbonyl as used herein refers to —C(O)OR in which R is alkyl, preferably lower alkyl or aryl, preferably lower aryl.

Alkoxy and thioalkoxy refer to RO— and RS—, in which R is alkyl, preferably lower alkyl or aryl, preferably lower aryl.

When a particular group, such as phenyl or pyridyl is specified, this means that the group is unsubstituted or is substituted.

The compounds can be made as described in the above-cited and herein incorporated patents of which the following are preferred.

2-[4-(4-hydroxy-4-phenylpiperidino)-2,2-diphenylbutyryl]-piperidine;

4-{4-4-[4-hydroxy-4-(3-trifluoromethylphenyl) piperidino]-2,2-diphenylbutyryl}morpholine;

1-{4-[4-hydroxy-4-(3-trifluoromethylphenyl)-piperidino]-2,2-diphenylbutyl}piperidine;

4-(p-chlorophenyl)-4-hydroxy-N-N-trimethyl-α,α-diphenylpiperidine-1-butyramide;

4-(p-chlorophenyl)-4-hydroxy-N-N-dimethyl-α,α-diphenylpiperidine-1-butyramide[loperamide];

4-(p-chlorophenyl)-4-hydroxy-N-N-dimethyl-α,α-diphenylpiperidine-butyramide-1-N-oxide;

4-(3,4-dichlorophenyl)-N-N-diethyl-4-hydroxy-α,α-diphenylpiperidine-1-butyramide;

4-(3,4-dichlorophenyl)-4-hydroxy-N-N-dimethyl-α,α-diphenylpiperidine- 1-butyramide;

4-(4-chloro-3-trifluoromethylphenyl)-4-hydroxy-N-N-dimethyl-α,α-diphenylpiperidine-1-butyramide;

4-(p-fluorophenyl)-4-hydroxy-N-N-trimethyl-α,α-diphenylpiperidine-1-butyramide;

4-(p-bromophenyl)-4-hydroxy-N-N-dimethyl-α,α-diphenylpiperidine-1-butyramide;

1-{4-[4-(3,4-dichlorophenyl)-4-hydroxypiperidino]-2,2-diphenylbutyryl}pyrroldine;

4-(p-chlorophenyl)-N-ethyl-4-hydroxy-N-methyl-α,α-diphenylpiperidine-1-butyramide;

5-[1,1-diphenyl-3-(exo-5-hydroxy-2-azabicyclo[2,2.-2] oct-2-yl)-propyl ]-2-methyl-1,3,4-oxadiazole;

5-[1,1-diphenyl-3-(exo-5-acetoxy-2-azabicyclo[2.2.-2] oct-2-yl)-propyl ]-2-methyl-1,3,4-oxadiazole;

5-[1,1-diphenyl-3-(endo-5-acetoxy-2-azabicyclo[2.2.-2] oct-2-yl)-propyl ]-2-methyl-1,3,4-oxadiazole;

5- [1,1,1-diphenyl-3-(endo-5-hydroxy-2-azabicyclo[2.2.-2]oct-2-yl)-propyl]-2oxadiazole; 5-[1,1-diphenyl-3-(endo-6-acetoxy-2-azabicyclo[2.2.-2]oct-2-yl)-propyl ]-2-oxadiazole;

5-[1,1-diphenyl-3-(endo-6-hydroxy-2-azabicyclo[2.2.-2] oct-2-yl)-propyl ]-2-methyl-1,3,4-oxadiazole;

5-[1,1-diphenyl-3-(exo-6-acetoxy-2-azabicyclo[2.2.-2]oct-2-yl)-propyl]-2-methyl-1,3,4-oxadiazole;

5-[1,1-diphenyl-3-(exo-6-hydroxy-2-azabicyclo[2.2.-2]oct-2-yl)-propyl]-2-methyl-1,3,4-oxadiazole;

1-(3,3,3-triphenylpropyl)-4-phenyl-4-piperidinecarboxylic acid hydrochloride;

ethyl 1-(3,3,3-triphenylpropyl)-4-phenyl-4-piperidinecarboxylate;

potassium 1-(3,3,3-triphenylpropyl)-4-phenyl-4-piperidinecarboxylate;

sodium 1-(3,3,3-triphenylpropyl)-4-phenyl-4-piperidinecarboxylate;

1-[3,3-diphenyl-3-(2-pyridyl)propyl]-4-phenyl-4-piperidinecarboxylic acid hydrochloride;

sodium 1-[3,3-diphenyl-3-(2-pyridyl)propyl]-4-phenyl-4-piperidinecarboxylate;

ethyl 1-[3,3-diphenyl-3-(2-pyridyl)propyl]-4-phenyl-4-piperidinecarboxylate;

potassium 1-[3,3-diphenyl-3-(2-pyridyl)propyl]-4-phenyl-4-piperidinecarboxylate;

1-(3,3,3-triphenylpropyl)-4-phenyl-4-piperidinemethanol;

1-[3,3-diphenyl-3-(2-pyridyl)propyl-4-phenyl-4-piperidinemethanol;

1-(3,3,3-triphenylpropyl)-4-phenyl-4-acetoxymethyl-piperidine;

1-(3,3,3-triphenylpropyl)-4-phenyl-4-methoxymethyl-piperidine;

1-(3,3,3-triphenylpropyl)-4-(4-chlorophenyl)-4-piperidinemethanol;

1-[3-(p-chlorophenyl)-3,3-diphenylpropyl]-4(phenyl)-4-piperidinemethanol;

1-[3-(p-tolyl)-3,3-diphenylpropyl]-4-(phenyl)-4-piperidinemethanol;

1-[3-(p-bromophenyl)-3,3-diphenylpropyl]-4(phenyl)-4-piperidinemethanol;

1-[3,3-diphenyl-3-(4-pyridyl)-propyl]-4-phenyl-4-piperidinemethanol;

1-[3,3-diphenyl-3-(3-pyridyl)propyl]-4-phenyl-4-piperidinemethanol;

1-(3,3,3-triphenylpropyl)-4-phenyl-4-hexoxymethyl-piperidine;

1-(3,3,3-diphenylpropyl)-4-p-tolyl)-4-piperidinemethanol;

1-(3,3,3-triphenylpropyl)-4-(p-trifluoromethyl)-4-piperidinemethanol;

1-(3,3,3-triphenylbutyl)-4-(phenyl)-4-piperidinemethanol;

1-(3,3,3-triphenylpropyl)-4-(phenyl)-4-piperidinemethanol;

1-(3,3,3-triphenylpropyl)-4(phenyl)-4-methoxyethylpiperidine;

1-[3,3-diphenyl-3-(2-pyridyl)propyl]-4-phenyl-4-methoxyethylpiperidine;

1-(3,3,3-triphenylpropyl)-4-phenyl-4-pipenidinemethanol;

1-[3,3-diphenyl-3-(2-pyridyl)propyl]-4-phenyl-4-piperidinemethanol;

1-(3,3,3-triphenylpropyl)-4-phenyl-4-acetoxymethylpiperidine;

1-(3,3,3-triphenylpropyl)-4-phenyl-4-methoxymethylpiperidine;

1-(3,3,3-triphenylpropyl)-4-(chlorophenyl)-4-piperidinemethanol;

1-(3,3,3-triphenylpropyl)-4-hydroxy-4-benzylpiperidine and 1-(3,3,3-triphenylpropyl)-4-hydroxy-4-benzylpiperidine; hydrochloride;

1-(3,3,3-triphenylpropyl)-4-hydroxy-4-(p-chlorobenzyl)piperidine;

1-(3,3,3-triphenylpropyl)-4-hydroxy-4-(p-methylbenzyl)piperidine;

1-[3,3,3(2-pyridyl)propyl]-4-benzyl-4-hydroxypiperidine;

m-chlorophenylamidinourea;

p-chlorophenylamidinourea;

3,4-dichlorophenylaridinourea;

m-bromophenylamidinourea;

p-bromophenylamidinourea;

3,4-dibromo-phenylamidinourea;

3-chloro-4-bromophenylamidinourea;

3-bromo-4-chlorophenylamidinourea;

3-chloro-4-fluorophenylamidinourea;

3-bromo-4-fluorophenylamidinourea;

3-fluoro4-chlorophenylamidinourea;

2,6-dimethylphenylamidinourea;

2,6-diethylphenylamidinourea;

2-methyl-6-ethylphenylamidinourea;

2-methyl-6-methoxyphenylamidinourea;

2-methyl-6-ethoxyphenylamidinourea;

2-ethyl-6-methoxyphenylamidinourea;

2-ethyl-6-ethoxyphenylamidinourea;

3,4-dimethoxyphenylamidinourea;

3,4-dihydroxyphenylamidinourea;

3,4,5-trimethoxyphenylamidinourea;

3,4,5-trihydroxyphenylamidinourea;

2-[(2-methyl-3-aminophenyl)amino]-1-pyrroline, dihydrochloride;

2-[(2-methyl-3-acetamidophenyl)amino]-1-pyrroline, hydrochloride;

2-[(2-methyl-3-(ethoxycarbonylamino)phenyl-)amino]-1-pyrroline, hydrochloride;

2-(2,2-diphenylpentyl)- 1-azabicylo[2.2.2]octane;

2-(2,2-diphenylhexyl)-1-azabicylo[2.2.2]octane;

2-(2,2-diphenylpropyl)-1-azabicylo[2.2.2]octane;

2-(2,2-diphenyloctyl)-1-azabicylo[2.2.2]octane; and 2-(2,2-diphenylheptyl)-1-azabicylo[2.2.2]octane.

Of these compounds, loperamide, [4-(p-chlorophenyl)-4-hydroxy-N-N-dimethyl-α,α-diphenyl-1-piperidenebutyramide monochloride]

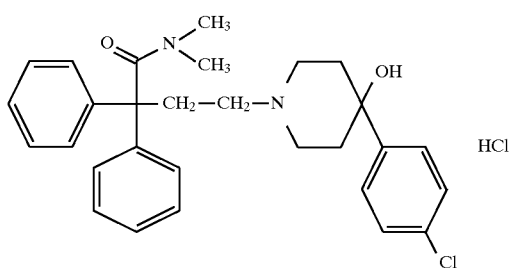

and the N-oxides of loperamide.

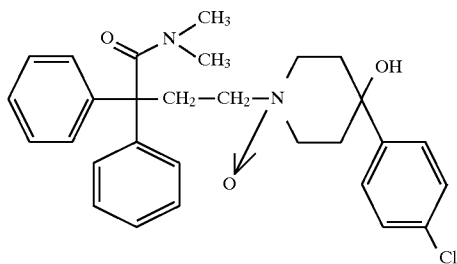

are most preferred.

FORMULATIONS OF THE PRESENT INVENTION

Effective concentrations of one or more of the compounds of the present invention or pharmaceutically acceptable derivatives thereof are mixed with a suitable pharmaceutical carrier or vehicle for systemic, topical or local administration. Compounds are included in an amount effective for reducing the pruritic symptoms for which treatment is contemplated. The concentration of active compound in the composition will depend on absorption, inactivation, excretion rates of the active compound, the dosage schedule, and amount administered as well as other factors known to those of skill in the art. For topical and local administration, the dosages are higher, typically at least about 5 to 10 fold, than the amount delivered when administered systemically orally.

The dosage of the compounds used in the compositions of the present invention is from about 0.001 to about 20 mg/kg body weight of the patient. Preferred unit dosages are from 0.05 to 10 mg/kg body weight of the patient.

The compounds contained in a pharmaceutically acceptable carrier are administered orally, parenterally, rectally and topically.

Pharmaceutical carriers or vehicles suitable for administration of the compounds and for the methods provided herein include any such carriers known to those skilled in the art to be suitable for the particular mode of administration.

a) Systemic Formulations

The formulations of the present invention are provided for administration to humans and animals in unit dosage forms, such as tablets, capsules, pills, powders, granules, sterile parenteral solutions or suspensions, and oral solutions or suspensions, and oil-water emulsions containing suitable quantities of a compound of Formula I or pharmacologically acceptable salts thereof.

Pharmaceutical dosage unit forms are prepared to provide from about 0.05 mg to about 500 mg and preferably from about 1.0 to about 200 mg of the essential active ingredient or a combination of essential ingredients per dosage unit form.

Oral pharmaceutical dosage forms are either solid or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Pharmaceutically acceptable carriers utilized in tablets are binders, lubricants, diluents, disintegrating agents, coloring agents, flavoring agents, and wetting agents. Enteric-coated tablets, due to their enteric-coating, resist the action of stomach acid and dissolve or disintegrate in the neutral or alkaline intestines. Sugar-coated tablets are compressed tablets to which different layers of pharmaceutically acceptable substances have been applied. Film-coated tablets are compressed tablets which have been coated with a water soluble polymers. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Examples of binders include glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Disintegrating agents include corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumia hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

Parenteral administration of the formulations of the present invention includes intravenous, subcutaneous and intramuscular administrations.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceliuose, hydroxypropyl methylcellulose and polyvinylpyrrolidone. Emulsifying agents include Polysorbate 80 (Tween 80). A sequestering or chelating agent of metal ions include EDTA. Pharmaceutical carriers also include ethyl alcohol polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule or a syringe with a needle.

All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

The pharmaceutically therapeutically active compounds of Formula I are administered orally, parenterally or rectally in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses which are not segregated in packaging.

b) Local and Topical Formulations

Typically a therapeutically effective dosage is formulated to contain a concentration of at least about 0.1% w/w up to about 50% w/w or more, preferably more than 1% w/w of the active compound to the treated tissue. The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the pruritic condition and may be empirically determined.

Compounds are typically included at concentrations 0.001% w/w or greater than 1% w/w up to 50% w/w or higher. The concentration is generally greater than the concentration for systemic administration of the compound. Preferable concentrations are in the range of 0.01% w/w to about 25% w/w, more preferably 1% w/w to 25% w/w, yet more preferably greater than about 1% w/w to about 10% w/w, and most preferably greater than 1% w/w up to about 5% w/w. Aqueous suspensions and formulations contain 1% w/w or more.

The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, or any other formulations suitable for topical or local administration.

The route of administration herein is topical or local administration, and compositions are formulated in a manner suitable for each route of administration. Preferred modes of administration include topical application to the skin, eyes or mucosa, and local application to the joints, such as by intra-articular injection. Thus, typical vehicles are those suitable for pharmaceutical or cosmetic application to body surfaces or for local injection.

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems.

For topical administration, the compounds may be formulated in compositions in the form of gels, creams, lotions, solids, solutions or suspensions, or aerosols. Compositions for treating human skin are formulated for topical application with an anti-pruritic effective amount of one or more of the compounds selected as described herein, in an effective concentration range [by weight], between about 0.1% and 80%, preferably 0.1 to 50%, more preferably greater than about 1% up to about 50% or more in a cream, ointment, lotion, gel, solution or solid base or vehicle known in the art to be non-toxic and dermatologically acceptable or suitable for application to the mucosa. Aqueous suspensions are preferably formulated at concentrations greater than about 1% w/w, more preferably 2% w/w.

To formulate a composition, the weight fraction of compound is dissolved, suspended, dispersed or otherwise mixed in a selected vehicle at an effective concentration such that the hyperalgesic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream [USP], and hydrophilic ointment [USP].

The choice of an acceptable vehicle is largely determined by the mode of application and tissue to be treated. Suitable pharmaceutically and dermatologically acceptable vehicles for topical application include those suited for use include lotions, creams, solutions, gels, tapes and the like. Generally, the vehicle is either organic in nature or an aqueous emulsion and capable of having the selected compound or compounds, which may be micronized, dispersed, suspended or dissolved therein. The vehicle may include pharmaceutically-acceptable emollients, skin penetration enhancers, coloring agents, fragrances, emulsifiers, thickening agents, and solvents.

For local internal administration, such as intra-articular administration, the compounds are preferably formulated as a suspension in an aqueous-based medium, such as isotonically buffered saline or are combined with a biocompatible support or bioadhesive intended for internal administration.

Lotions

The lotions contain an effective concentration of one or more of the compounds. The effective concentration is preferably effective to deliver an anti-pruritic amount, typically at a concentration of between about 0.1–50% w/w or more of one or more of the compounds provided herein. The lotions also contain from 1% to 50% w/w, preferably from 3% to 15% w/w of an emollient and the balance water, a suitable buffer, a $C_2$ or $C_3$ alcohol, or a mixture of water of the buffer and the alcohol. Any emollients known to those of skill in the art as suitable for application to human skin may be used. These include, but are not limited to, the following:

(a) Hydrocarbon oils and waxed, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil and soybean oil.

(d) Acetoglyceride esters, such as acetylated monoglycerides.

(e) Ethoxylated glycerides, such as ethoxylated glyceryl monostearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate diisopropyl adipate, diisohexyl adipate, dihexyldecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to pelargonic, lauric, myristic, palmitic, stearic, isostearic, hydroxystearic, oleic, linoleic, ricinoleic, arachidonic, behenic, and erucic acids.

(i) Fatty alcohols having 10 to 20 carbon atoms, such as but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to, ethoxylated fatty alcohols of 10 to 20 carbon atoms, such as, but are not limited to, the lauryl cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol [M.W. 2000–4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly)ethylene oxide) homopolymers [M.W. 100,000–5,000,000], polyalkylene glycols and derivatives, hexylene glycol (2-methyl-2,4-pentanediol), 1,3-butylene glycol, 1,2,6-hexanetriol, ethohexadiol U.S. Pat. No. (2-ethyl-1,3-hexanediol), hexanediol), $C_{15}$–$C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and di-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di- fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain from 1% w/w to 10% w/w, more preferably from 2% w/w to 5% w/w, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxides mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol sorbitan, polyoxyethylene sorbitol, polyoxyethylene sorbitan and hydrophilic wax esters. Suitable anionic emulsifiers include, but are not limited to, the fatty acid soaps, e.g. sodium, potassium and triethanolamine soaps, wherein the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably, the compound, is dissolved, suspended or otherwise uniformly dispersed in the mixture.

Other conventional components of such lotions may be included. One such additive is a thickening agent at a level from 1% to 10% w/w of the composition. Examples of suitable thickening agents include, but are not limited to: cross-linked carboxypolymethylene polymers, ethyl cellulose, polyethylene glycols, gum, tragacanth, gum kharaya, xanthan gums and bentonite, hydroxyethyl cellulose, and hydroxypropyl cellulose.

Creams

The creams are formulated to contain concentration effective to deliver an anti-pruritic effective amount of the compound to the treated tissue, typically at between about 0.1%, preferably at greater than 1% up to and greater than 50%, preferably between about 3% and 50%, more preferably between about 5% and 15% of one or more of the compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

Solutions and suspensions for topical and local administration

The solutions are formulated to contain an amount of one or more compounds effective to deliver an anti-pruritic amount, typically at a concentration of between about 0.1–50% w/w, preferably at least more than 1% w/w, more preferably more than 2% w/w of one or more of the compounds provided herein. The balance is water, a suitable organic solvent or other suitable solvent or buffer. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol isopropanol, diethyl tartrate, butanediol and mixtures thereof. Such solvent systems can also contain water.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating magnets, such as ethylenediaminetetraacetic acid [EDTA]; buffers, such as acetates, citrates and phosphates; and agents for the adjustment of tonicity such as sodium chloride or dextrose. Liquid preparations can be enclosed in ampoules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or may be formulated as an aerosol or foam and applied to the skin as a spray-on. The aerosol compositions typically contain from 25% to 80% w/w, preferably from 30% to 50% w/w, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspension may also be topically applied to the eyes and mucosa. Solutions, particularly those intended for opthalmic use, may be formulated as 0.01%–10% w/w isotonic solutions, pH about 5–7, with appropriate salts, and preferably containing one or more of the compounds herein at a concentration of about 0.1% w/w preferably greater than 1% w/w, up to 50% w/w or more. Suitable opthalmic solutions are known [see, e.g. U.S. Pat. No. 5,116,868, which describes typical compositions of opthalmic irrigation solutions and solutions for topical application]. Such solutions, which have a pH adjusted to about 7.4, contain, for example, 90–100 mM sodium chloride, 4–6 mM dibasic potassium phosphate, 4–6 MM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The active compounds of the present invention can also be mixed with other active materials, that do not impair the desired action, or with materials that supplement the desired action, including viscoelastic materials, such as hyaluronic acid, which is sold under the trademark HEALON [solution of a high molecular weight (MW of about 3 million) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803], VISCOAT [fluorine-containing (meth)acrylates, such as, 1H, 2H, 2H-heptadecafluorodecylmethacrylate; see, e.g., U.S. Pat. .Nos. 5,278,126, 5,273,751 and 5,214,080; commercially available from Alcon Surgical, Inc.], ORCOLON [see, e.g., U.S. Pat. Nos. 5,273,056; commercially available from Optical Radiation Corporation], methylcellulose, methyl hyaluronate, polyacrylamide and polymethacrylamide [see, e.g., U.S. Pat. No. 5,273,751]. The viscoelastic materials are present generally in amounts ranging from about 0.5 to 5.0% w/w, preferably 1 to 3% w/w of the conjugate material and serve to coat and protect the treated tissues. The compositions may also include a dye, such as methylene blue or other inert dye, so that the composition can be seen when injected into the eye or contacted with the surgical site during surgery.

Gels

Gel compositions can be formulated by simply admixing a suitable thickening agent to the previously described solution or suspension composition. Examples of suitable thickening agents have been previously described with respect to the lotions.

The gelled compositions contain an effective amount of one or more of an anti-pruritic amount, typically at a concentration of between about 0.1–50% w/w or more of one or more of the compounds provided therein; from 5% to 75% w/w preferably from 10% to 50% w/w, of an organic solvent as previously described; from 0.5% to 20% w/w, preferably from 1% to 10% w/w of the thickening agent; the balance being water or other aqueous carrier.

Solids

Compositions of solid forms may be formulated as stick-type compositions intended for application to the lips or other parts of the body. Such compositions contain an effective amount of one or more of the compounds provided therein. The amount is typically an amount effective to deliver an anti-pruritic amount, typically at a concentration of between about 0.1–50% w/w or more of one or more of the compounds provided herein. The solids also contain from about 40% to 98% w/w, preferably from about 50% to 905 w/w, of the previously described emollients. This composition can further contain from 1% to 20% w/w, preferably from 5% to 15% w/w, of a suitable thickening agent, and, if desired or needed, emulsifiers and water or buffers. Thickening agents previously described with respect to lotions are suitably employed in the composition in solid form.

Other ingredients such as preservatives, including methyl-paraben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

The following examples are included for illustrative purposes only and are not intended to limit the scope of the invention.

Example 1

Capsules

| | |
|---|---|
| Active Compound | 2.5 gm |
| Corn starch | 23.0 gm |
| Lactose | 145.0 gm |
| Talc | 15.0 gm |
| Magnesium stearate | 3.0 gm |

The ingredients were mixed and were encapsulated using techniques practiced in the art.

Example 2

Tablet

| | |
|---|---|
| Active Compound | 150 gm |
| Lactose | 125 gm |

-continued

| | |
|---|---|
| Corn starch | 50 gm |
| Magnesium stearate | 2.0 gm |
| Liquid Petrolatum | 2.0 gm |

The ingredients were mixed, then put through U.S. Standard Screens to produce fine granules. The granules were compressed into tablets, each tablet containing about 150 mg of an active compound of the present invention.

Example 3

Syrup

| | |
|---|---|
| Active Compound | 25 gm |
| Lemon Oil | 2 ml |
| Sucrose | 650 gm |
| Citric Acid | 4 gm |
| Benzoic Acid | 3 gm |
| Tragacanth | 16 gm |
| Deionized water q.s. | 1000 ml |

The ingredients, without the active compound, are dispersed in water to make about 800 to 900 ml of solution. The active compound is then added and the solution is stirred into a syrup. Water is then added to make 1000 ml of the syrup.

Example 4

Parenteral Solution

| | |
|---|---|
| Active Compound | 39 gm |
| Methylparaben | 3 gm |
| Propylparaben | 1 gm |
| Lidocaine | 5 gm |
| Deionized water q.s. | 1000 ml |

The ingredients are dissolved in water to provide a solution followed by sterilization by filtration.

Example 5

Rectal Suppository

| | |
|---|---|
| Active Compound | 80 gm |
| Propylene glycol | 95 gm |
| Polyethylene glycol 4000 | 1800 gm |

The active compound is added to the propylene glycol and milled until a finely divided uniform mixture is formed. The polyethylene glycol 4000 is melted and the propylene glycol dispersion is added with stirring to obtain a suspension. The suspension is poured into molds, allowed to solidify and removed from the molds for packaging.

Example 6

Water-washable ointment

| | |
|---|---|
| Active Compound | 1.4% w/w |
| Lanolin alcohol | 0.15 w/w |
| Emulsifying wax NF | 7.5% w/w |
| PEG-20 glycerides | 5.0% w/w |
| Petrolatum | 86.0% w/w |

The ingredients are melted together and mixed well until the resulting ointment congeals.

Example 7

Oil-in-water cream

| | |
|---|---|
| Active Compound | 10.0% w/w |
| Benzyl alcohol | 4.0% w/w |
| Propylene glycol | 10.0% w/w |
| Polyethylene glycol 400 | 10.0% w/w |
| Petrolatum | 20.0% w/w |
| Stearyl alcohol | 10.0% w/w |
| Poloxamer | 10.0% w/w |
| Water q.s. | 100 |
| Buffer to pH | 7.0% w/w |

In preparing the oil-in-water cream, water, propylene glycol and polyethylene glycol 400 are heated to about 70° to 80° C., followed by adding a mixture of petrolatum, stearyl alcohol and poloxamer and the mixture is stirred until homogeneous. The active compound in benzyl alcohol is added and the mixture is homogenized. The pH is then adjusted with a buffer to about 7.0.

Example 8

Aqueous gel

| | |
|---|---|
| Active Compound | 10.0% w/w |
| Benzyl alcohol | 4.0% w/w |
| Hydroxyethyl cellulose | 3.0% w/w |
| Water q.s. | 100 |
| Buffer to pH | 7.0% w/w |

TESTING OF THE FILM-FORMER COMPOSITIONS FOR ANTI-PRURITIC ACTIVITY

Testing was performed in a mouse scratch model under blind conditions.

Groups of 8–10 male Swiss albino mice (Hilltop Lab Animals, Inc., Scottsdale, Pa.), weighing 2.5–2.6 g, were used in the testing. They were housed under controlled temperature of 23°–25° C. Food and water were freely available. Before the experiments, the mice were weighed, put into individual boxes and allowed to acclimate for 30 min.

Materials

Vehicle used to dissolve the test compounds: 20% w/w cremophor EL.

To induce scratching Compound 48/80 (Sigma, St. Louis, USA) was used which has been shown to produce an itch sensation in humans (Armstrong et al., J. of Physiol., 120: 326, 1953).

The compounds to be tested for anti-pruritic activity were dissolved in the vehicle of 20% w/w cremophor EL.

Method

100 $\mu$l of the vehicle (3–5 doses, n=8–10) was injected s.c. into the back of the neck of mice 20 min. before challenging them with 100 $\mu$l of Compound 48/80 (2 mg/ml; 50 $\mu$g) injected s.c. into the back of the neck. One minute later the mice were observed for 30 min. and the number of hindleg scratching movements directed to the neck was counted.

The vehicle-injected mice scratched 79±16 times in the 30 min after the standard challenge with Compound 48/80.

To each mouse of a group of 8–10 mice previously subjected to the standard challenge various doses of the compounds, to be tested for anti-pruritic activity, were administered s.c. into the back of the neck. One minute later the mice were observed for 30 min and the number of hindleg scratching movements directed to the neck was counted.

For each group of 8–10 mice, the mean values for scratching were normalized to relative % antagonism of scratching and then plotted vs. dose of test compounds.

Interval estimates of mean $A_{50}$ were determined by nonlinear regression analysis (Kaleida Graph) and mean % inhibition of scratching was calculated.

The following compounds were tested:
(1) 1-[3,3-diphenyl-3-(2-pyridyl)propyl]-4-phenyl-4-piperidinecarboxylic acid hydrochloride;
(2) 1-(3,3,3-triphenylpropyl)-4-hydroxy-4-p-chlorobenzylpiperidine; and
(3) 4(p-chlorophenyl-4-hydroxy-N-N-dimethyl-α,α-diphenylpiperidine-1-butyramide[loperamide].

Each compound (1,2,3) antagonized Compound 48/80-induced scratching in a dose-related manner. Results are shown in Table C.

TABLE C

| Compound | Dose (mg/kg, s.c.) | Mean % Inhibition |
|---|---|---|
| (1) | 2.5 | 32 |
| | 5.0 | 65 |
| | 10.0 | 83 |
| (2) | 1.0 | 35 |
| | 2.5 | 68 |
| | 5.0 | 94 |
| (3) | 0.5 | 18 |
| | 1.0 | 47 |
| | 2.5 | 65 |

Mean % Inhibition of Scratching

Other compounds tested have shown similar anti-pruritic, dose-responsive activity in the range of from about 15 to about 95% based on doses of form about 0.5 to 10.0 mg/kg, s.c.

It should be understood by those skilled in the art that, while the invention has been described and illustrated above in connection with certain specific embodiments, many variations and modifications may be employed without departing from the scope of the invention.

What is claimed is:

1. A method of preventing or treating a non-respiratory and non-analis pruritic condition in a mammal in need of such prevention or treatment comprising topically, orally or parenterally administering to said mammal an effective anti-pruritic amount of a pharmaceutical composition which stimulates opiate receptors on peripheral sensory neurons in the skin comprising a compound of formula I

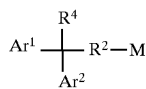

wherein M is

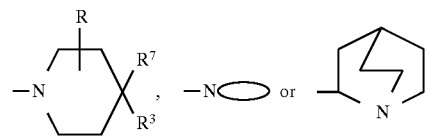

wherein:

is an azabicycloalkyl containing from 6 to 9 carbon atoms with at least 5 atoms in each ring and is unsubstituted or substituted with $OR^{18}$ in which $R^{18}$ is hydrogen or lower alkanoyl containing 2 to 7 carbons and $OR^{18}$ is at the 5 position in 5-membered rings or the 5 or 6 position in 6-membered rings and is attached in the endo or exo configuration;

$Ar^1$ and $Ar^2$ are either (i) or (ii) as follows:
(i) each is independently selected from aryl and heteroaryl groups containing from 5 to 7 members in the ring, each is unsubstituted or substituted with one or more substituents selected from halo, haloalkyl, hydroxy, alkyl, alkyloxy, aminosulfonyl, alkylcarbonyl, nitro, haloalkyl, trifluoromethyl, amino, aminocarbonyl, phenylcarbonyl or thienyl, where the alkyl groups are straight or branched chains lower alkyl containing from 1 to 6 carbon atoms; or
(ii) $Ar^1$ and $Ar^2$ are each independently phenyl or pyridyl groups and with the carbon to which they are commonly linked form a fused ring so that the compounds of formula (I) have the structure:

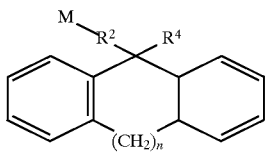

wherein n is 0 to 3;
$R^2$ is either alkyl in which the alkyl group is a straight or branched chain having 1 to 12 carbon atoms, or is alkylene having 1 to 6 carbon atoms with one or two double bonds;
$R^3$ is $Ar^3$,—Y—$Ar^3$, where Y is alkylene or alkyl having 1 to 3 carbon atoms, or is

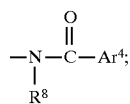

$R^8$ is hydrogen or alkyl that is a straight or branched chain containing from 1 to 6 carbon atoms;
$Ar^3$ is aryl or heteroaryl containing from 5 to 7 members in the ring, which is unsubstituted or substituted with one or more substituents of halo, halo lower alkyl or lower alkyl;
$Ar^4$ is either:
(i) is a heterocycle containing one to three fused rings or which is unsubstituted or substituted with one or more substituents selected from halo, halo lower alkyl or lower alkyl, or
(ii) $Ar^4$ is a radical of formula:

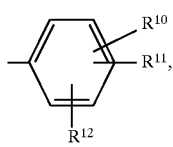

in which $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_3$–$C_6$ alkenyloxy, arylalkyloxy, aryloxy or alkyl, in which each group is unsubstituted or substituted with one or more halo atoms, halo alkyl or alkyl, and the alkyl groups are straight or branched chains that are lower alkyl;
R is hydrogen, alkyl, halo, haloalkyl or $OR^9$;
$R^9$ is selected from alkyl, arylalkyl, alkylcarbonyl, aminoalkyl, alkylaminoalkyl or dialkylaminoalkyl, in which the alkyl groups are straight or branched chains containing 1 to 12 carbon atoms;

R⁴ is selected from among:
(i) 5- to 7-membered aryl groups, which are unsubstituted or substituted with lower alkyl, halo lower alkyl or halo, or
(ii) heterocyclic rings, containing one to three heteroatoms, that are unsubstituted or substituted with halo, halo lower alkyl or lower alkyl, or
(iii) alkyl containing from 1 to 8 carbon atoms, alkenyl containing 3 to 6 carbon atoms, cycloalkyl containing from 3 to 6 carbon atoms, cycloalkyl alkyl in which the first alkyl contains 3 to 6 carbons and the second containing 1 to 3 carbons, or cycloalkenyl containing 4 to 7 carbons, or

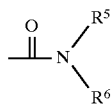  (iv)

where R⁵ and R⁶ are either:
(i) independently selected from hydrogen, alkyl, which is a straight or branched chain containing 1 to 12 carbon atoms, alkenyl, which is straight or branched chain, containing 1 to 12 carbon atoms and one or two double bonds, or aryl, which contains 5 to 7 carbon atoms, or
(ii) R⁵ and R⁶ are selected from carbon chains, heteroatoms, and carbon chains containing one or more heteroatoms, so that with the nitrogen atoms to which each is attached they form a 3- to 7-membered heterocyclic ring containing one to three heteroatoms that is unsubstituted or substituted with halo, halo lower alkyl or lower alkyl; and R⁷ is selected from among:
H;
OH;
—R¹⁴OR¹³ in which R¹³ is hydrogen or lower alkyl, alkanoyl containing 2 to 5 carbon atoms, and R¹⁴ is lower alkenyl or lower alkyl;
—CH₂NR¹⁵R¹⁶ in which R¹⁵ is hydrogen, lower alkyl or lower alkanoyl and R¹⁶ is hydrogen or lower alkyl;
OR¹⁵;
R²²OR¹³, in which R²² is lower alkyl;
—C(O)OR¹⁷ in which R¹⁷ is hydrogen, alkyl containing form 1 to 7 carbons or alkenyl having 3–7 carbon atoms, aryl or heteroaryl; or an alkali metal or alkaline earth metal salt, in a pharmaceutically acceptable carrier.

2. The method of claim 1 wherein said compound is selected from the group consisting of:
2-[4-(4-hydroxy-4-phenylpiperidino)-2,2-diphenylbutyryl]-piperidine;
4- {4-[4-hydroxy-4-(3-trifluoromethylphenyl)piperidino]-2,2-diphenylbutyryl}morpholine;
1- {4-[4-hydroxy-4-(3-trifluoromethylphenyl)-piperidino]-2,2-diphenylbutyl}piperidine;
4-(p-chlorophenyl)-4-hydroxy-N-N-trimethyl-α-α-diphenylpiperidine-1-butyramide;
4-(p-chlorophenyl)-4-hydroxy-N-N-dimethyl-α-α-diphenylpiperidine-1-butyramide;
4-(p-chlorophenyl)-4-hydroxy-N-N-dimethyl-α-α-diphenylpiperidine-butyramide-1-N-oxide;
4-(3,4-dichlorophenyl)-N-N-diethyl-4-hydroxy-α-α-diphenylpiperidine-1-butyramide;
4-(3,4-dichlorophenyl)-4-hydroxy-N-N-dimethyl-α-α-diphenylpiperidine-1-butyramide 4-(4-chloro-3-trifluoromethylphenyl)-4-hydroxy-N-N-dimethyl-α-α-diphenylpiperidine-1-butyramide;
4-(p-fluorophenyl)-4-hydroxy-N-N-,y-trimethyl-α-α-diphenylpiperidine-1-butyramide;
4-(p-bromophenyl)-4-hydroxy-N-N-dimethyl-α-α-diphenylpiperidine-1-butyramide;
1- {4-[4-(3,4-dichlorophenyl)-4-hydroxypiperidino]-2,2-diphenylbutyryl}pyrrolidine;
4-(p-chlorophenyl)-N-ethyl-4-hydroxy-N-methyl-α-α-diphenylpiperidine-1-butyramide;
5-[1,1-diphenyl-3-(exo-5-hydroxy-2-azabicyclo [2,2.-2] oct-2-yl)-propyl]-2-methy-1,3,4-oxadiazole;
5-[1,1-diphenyl-3-(exo-5-acetoxy-2-azabicyclo[2.2.-2] oct-2-yl)-propyl ]-2-methyl-1,3,4-oxadiazole;
5-[1,1-diphenyl-3-(endo-5-acetoxy-2-azabicyclo[2.2.-2] oct-2-yl)-propyl ]-2-methyl-1,3,4-oxadiazole;
5-[1,1-diphenyl-3-(endo-5-hydroxy-2-azabicyclo [2.2.-2] oct-2-yl)-propyl ]-2-methyl-1,3,4-oxadiazole;
5-[1, 1-diphenyl-3-(endo-6-acetoxy-2-azabicyclo[2.2.-2] oct-2-yl)-propyl ]-2-methyl-1,3,4-oxadiazole;
5-[1,1-diphenyl-3-(endo-6-hydroxy-2-azabicyclo[2.2.-2] oct-2-yl)-propyl ]-2-methyl-1,3,4-oxadiazole;
5-[1,1-diphenyl-3-(exo-6-acetoxy-2-azabicyclo[2.2.-2] oct-2-yl)-propyl ]-2-methyl-1,3,4-oxadiazole;
5-[1,1 -diphenyl-3-(exo-6-hydroxy-2-azabicyclo[2.2.-2] oct-2-yl)-propyl ]-2-methyl-1,3,4-oxadiazole;
1-(3,3,3-triphenylpropyl)-4-phenyl-4-piperidinecarboxylic acid hydrochloride;
ethyl 1-(3,3,3-triphenylpropyl)-4-phenyl-4-piperidinecarboxylate;
potassium 1-(3,3,3-triphenylpropyl)-4-phenyl-4-piperidinecarboxylate;
sodium 1-(3,3,3-triphenylpropyl)-4-phenyl-4-piperidinecarboxylate;
1-[3,3-diphenyl-3-(2-pyridyl)propyl]-4-phenyl-4-piperidinecarboxylic acid hydrochloride;
sodium 1-[3,3-diphenyl-3-(2-pyridyl)propyl]-4-phenyl-4-piperidinecarboxylate;
ethyl 1-[3,3-diphenyl-3-(2-pyridyl)propyl]-4-phenyl-4-piperidinecarboxylate;
potassium 1-[3,3-diphenyl-3-(2-pyridyl)propyl]-4-phenyl-4-piperidinecarboxylate;
1-(3,3,3-triphenylpropyl)-4-phenyl-4-piperidinemethanol;
1-[3,3-diphenyl-3-(2-pyridyl)propyl]-4-phenyl-4-piperidinemethanol;
1-(3,3,3-triphenylpropyl)-4-phenyl-4-acetoxymethyl-piperidine;
1-(3,3,3-triphenylpropyl)-4-phenyl-4-methoxymethyl-piperidine;
1-(3,3,3-triphenylpropyl)-4-(4-chlorophenyl)-4-piperidinemethanol;
1-[3-(p-chlorophenyl)-3,3-diphenylpropyl]-4-(phenyl)-4-piperidinemethanol;
1-[3-(p-tolyl)-3,3-diphenylpropyl]-4-phenyl)-4-piperidinemethanol;
1-[3-(p-bromophenyl)-3,3-diphenylpropyl]-4-(phenyl)-4-piperidinemethanol;
1-[3,3-diphenyl-3-(4-pyridyl)-propyl]-4-phenyl-4-piperidinemethanol;

1-[3,3-diphenyl-3-(3-pyridyl)propyl]-4-phenyl-4-piperidinemethanol;
1-(3,3,3-triphenylpropyl)-4-phenyl-4-hexoxymethyl-piperidine;
1-(3,3,3-triphenylpropyl)-4-(p-tolyl)-4-piperidinemethanol;
1-(3,3,3-triphenylpropyl)-4-(p-trifluoromethyl)-4-piperidinemethanol;
1-(3,3,3-triphenylbutyl)-4-(phenyl)-4-piperidinemethanol;
1-(3,3,3-triphenylpropyl)-4-(phenyl)-4-piperidinemethanol;
1-(3,3,3-triphenylpropyl)-4-(phenyl)-4-methoxyethylpiperidine;
1-[3,3-diphenyl-3-(2-pyridyl)propyl]-4-phenyl-4-methoxyethylpiperidine;
1-(3,3,3-triphenylpropyl)-4-phenyl-4-piperidinemethanol;
1-[3,3-diphenyl-3-(2-pyridyl)propyl]-4-phenyl-4-piperidinemethanol;
1-(3,3,3-triphenylpropyl)-4-phenyl-4-acetoxymethylpiperidine;
1-(3,3,3-triphenylpropyl)-4-phenyl-4-methoxymethylpiperidine;
1-(3,3,3-triphenylpropyl)-4-(chlorophenyl)-4-piperidinemethanol;
1-(3,3,3-triphenylpropyl)-4-hydroxy-4-benzylpiperidine and 1-(3,3,3-triphenylpropyl)-4-hydroxy-4-benzylpiperidine hydrochloride;
1-(3,3,3-triphenylpropyl)-4-hydroxy-4-p-chlorobenzylpiperidine;
1-(3,3,3-triphenylpropyl)-4-hydroxy-4-p-methylbenzylpiperidine;
1-[3,3,3-(2-pyridyl)propyl]-4-benzyl-4-hydroxypiperidine hydrochloride;
m-chlorophenylamidinourea;
p-chlorophenylamidinourea;
3,4-dichlorophenylamidinourea;
m-bromophenylamidinourea;
p-bromophenylamidinourea;
3,4-dibromo-phenylamidinourea;
3-chloro-4-bromophenylamidinourea;
3-bromo-4-chlorophenylamidinourea;
3-chloro-4-fluorophenylamidinourea;
3-bromo-4-fluorophenylamidinourea;
3-fluoro-4-chlorophenylamidinourea;
2,6-dimethylphenylamidinourea;
2,6-diethylphenylamidinourea;
2-methyl-6-ethylphenylamidinourea;
2-methyl-6-methoxyphenylamidinourea;
2-methyl-6-ethoxyphenylamidinourea;
2-ethyl-6-methoxyphenylamidinourea;
2-ethyl-6-ethoxyphenylamidinourea;
3,4-dimethoxyphenylamidinourea;
3,4-dihydroxyphenylamidinourea;
3,4,5-trimethoxyphenylamidinourea;
3,4,5-trihydroxyphenylamidinourea;
2-[(2-methyl-3-aminophenyl)amino]-1-pyrroline, dihydrochloride;
2-[(2-methyl-3-acetamidophenyl)amino]-1-pyrroline, hydrochloride;
2-[(2-methyl-3-(ethoxycarbonylamino)phenyl-)amino]-1-pyrroline, hydrochloride;
2-(2,2-diphenylpentyl)-1-azabicylo[2.2.2]octane;
2-(2,2-diphenylhexyl)-1-azabicylo[2.2.2]octane;
2-(2,2-diphenylpropyl)-1-azabicylo[2.2.2]octane;
2-(2,2-diphenyloctyl)-1-azabicylo[2.2.2]octane; and
2-(2,2-diphenylheptyl)-1 -azabicylo[2.2.2]octane, or a salt thereof, in a pharmaceutically acceptable carrier.

3. The method of claim 1 wherein said non-respiratory pruritic condition is selected from the group consisting of urticaria, ded-natitis, psoriasis, eczema dermal myiasis, pediculoses enterobiasis onchocersiasis and alkokinesis.

* * * * *